United States Patent [19]

Butterfield et al.

[11] Patent Number: 5,158,091
[45] Date of Patent: Oct. 27, 1992

[54] TONOMETRY SYSTEM FOR DETERMINING BLOOD PRESSURE

[75] Inventors: Robert D. Butterfield, Poway; Kenneth J. Pytel; Charles R. Holdaway, both of San Diego; Stephen A. Martin, Carlsbad, all of Calif.

[73] Assignee: IVAC Corporation, San Diego, Calif.

[21] Appl. No.: 621,165

[22] Filed: Nov. 30, 1990

[51] Int. Cl.⁵ .............................................. A61B 5/021
[52] U.S. Cl. ................... 128/672; 128/687; 128/748
[58] Field of Search ................. 128/687–690, 128/633, 634, 748, 672

[56] References Cited

U.S. PATENT DOCUMENTS

| | | | |
|---|---|---|---|
| 3,517,999 | 6/1970 | Weaver | 128/687 X |
| 3,782,368 | 1/1974 | Reibold | 128/687 |
| 3,991,746 | 11/1976 | Hanna | 128/687 X |
| 4,085,740 | 4/1978 | Allen, Jr. | 128/687 X |
| 4,307,728 | 12/1981 | Walton | 128/687 |
| 4,712,566 | 12/1987 | Hök | 128/748 |
| 4,727,730 | 3/1988 | Boiarski et al. | 128/667 |
| 4,753,243 | 6/1988 | Mawhinney et al. | 128/687 |
| 4,803,992 | 2/1989 | Lemelson | 128/634 |
| 4,901,733 | 2/1990 | Kaida et al. | 128/687 |
| 5,085,223 | 2/1992 | Lars et al. | 128/675 |

Primary Examiner—William E. Kamm
Assistant Examiner—Kevin Pontius
Attorney, Agent, or Firm—Dykema Gossett

[57] ABSTRACT

A tissue contact stress sensing system incorporates a semiconductor assembly and a continuous diaphragm to noninvasively determine the intra-arterial blood pressure of a patient. The system comprises a continuous diaphragm placed against a patient's tissue which covers an underlying artery. The semiconductor assembly is placed in close proximity to and spaced apart from the diaphragm for directly irradiating the diaphragm with electromagnetic radiation and receiving a portion of the electromagnetic radiation which is reflected from the continuous diaphragm. The disclosed system also utilizes a technique for minimizing the system errors associated with temperature drift and aging of the sensor.

57 Claims, 4 Drawing Sheets

TONOMETRY SYSTEM FOR DETERMINING BLOOD PRESSURE

TECHNICAL FIELD

The present invention generally relates to a pressure measurement system, and more particularly relates to a system for noninvasively determining the blood pressure of a patient by detecting the surface stress of tissue above an arterial vessel.

BACKGROUND OF THE INVENTION

Systems for determining the intra-arterial blood pressure of a patient can be subdivided into two main groups-those which invade the arterial wall to directly access blood pressure and those which use non invasive techniques. For a long period of time, the most accurate blood pressure measurements were achievable only by use of invasive methods. One such common method involved use of a fluid filled catheter inserted into the patient's artery.

While invasive methods provide for accurate blood pressure measurements, the risk of infection and potential for complications, in many cases, outweigh the advantages of using invasive methods. Because of the risk of complication associated with invasive methods, a noninvasive method, known as the Korotkoff method is widely used. The Korotkoff method is known as an auscultatory method because it uses the characteristic sound made as the blood flows through the artery to denote the high and low blood pressure points. Although the Korotkoff method is noninvasive, it only provides a measurement of the highest blood pressure (systolic) and the lowest blood pressure (diastolic) along the continuous pressure wave form. While systolic and diastolic pressure are often sufficient for accurate diagnosis, there are many applications in which it is desirable to use the entire curve of the blood pressure wave form. In these applications, the Korotkoff method simply is incapable of providing satisfactory information. In addition to this limitation of the Korotkoff method, it necessitates the temporary occlusion of the artery in which blood pressure is being monitored. While arterial occlusion is not prohibited in many applications, there are occasions where the patient's blood pressure must be monitored continuously (such as when undergoing surgery) and accordingly, prohibiting blood flow, even on a temporary basis, is undesirable or unacceptable. Other problems associated with the Korotkoff method include the fact that the cuff must be properly sized with respect to the patient and the detrimental affects of respiration and acoustic noise on overall measurement accuracy.

Because of the above mentioned risks involved with invasive blood pressure measurement, and the shortcomings of the Korotkoff method, extensive investigation has been conducted in the area of continuous, noninvasive blood pressure monitoring and recording methods. Many of these noninvasive techniques make use of tonometric principles which center around the fact that as blood flows through the arterial vessel, forces are transmitted through the artery wall and through the surrounding arterial tissue and are accessible for monitoring. Because the tonometric method of determining blood pressure is noninvasive, it is used without the risks associated with invasive techniques. Furthermore, since it does not suffer from the limitations of the auscultatory method, it has the capability of reproducing the entire blood pressure wave form, as opposed to the limited systolic and diastolic pressure points provided by the Korotkoff method.

In several of the prior art arterial tonometers, a row of individual transducer elements, such as strain gauges or the like, are placed in direct contact with the tissue which overlays an arterial vessel from which blood pressure is to be measured. As the blood pressure within the arterial vessel increases and decreases the vessel wall expands and contracts thereby transmitting forces through the overlying tissue and onto the row of transducer elements. Although the individual elements are dimensionally sized so that several are required to cover the entire diameter of the underlying arterial vessel, their discrete character prevents reconstructing a true continuous contour of the tissue stresses which occur across the entire row of elements.

It has also been found that many prior art tonometry sensors are cumbersome, difficult to administer and uncomfortable to wear for any long period of time.

Thus, it is desirable to provide a noninvasive tonometry system for determining the blood pressure in an arterial vessel by measuring the stress of the tissue overlaying the arterial vessel.

Still further, it is desirable to have a system which is capable of accurately reconstructing a continuous stress contour across the diameter of an artery of interest.

It is also desirable to have a system which automatically compensates for errors introduced into the tissue stress signal which result from temperature, aging or other factors which influence the tissue stress sensor.

Additionally, it is desirable to have a miniaturized sensor which can be easily administered and comfortably worn for long periods of time.

SUMMARY OF THE INVENTION

In light of the foregoing objects, the present invention provides a tissue contact stress sensor for use in a system for noninvasively determining the intra-arterial blood pressure of a patient. The tissue contact stress sensor comprises a continuous diaphragm for placing against a patient's tissue which covers an underlying artery. The diaphragm is adapted to be deformed in response to stresses in the tissue created by the arterial blood pressure within the underlying artery. A semiconductor assembly is placed in close proximity to and spaced apart from the continuous diaphragm. The semiconductor assembly irradiates the diaphragm with electromagnetic radiation and receives a portion of the electromagnetic radiation which is reflected from the continuous diaphragm. The quantity of electromagnetic radiation which is received by the semiconductor assembly is a function of the stress experienced by the tissue overlaying the artery. Under controlled conditions, intra-arterial blood pressure can be determined by measuring the stress of the tissue overlaying the artery. Because the semiconductor assembly performs both the irradiating and receiving function, it allows the tissue contact stress sensor to be miniaturized and allows the semiconductor assembly to be placed very close to the continuous diaphragm. In a preferred embodiment, the diaphragm is comprised of silicon and includes a silicon base having a longitudinal trough therein. The cross-sectional profile of the trough generally resembles a tetragonal-pyramidal geometry. The trough bottom is generally planar and is preferably coated with a material for reflecting the electromagnetic radiation irradiated by the semiconductor assembly.

The sensing apparatus preferably includes a spacing element disposed between the diaphragm and the semiconductor assembly for providing fixed alignment and positioning of the semiconductor assembly in relation to the diaphragm. Preferably the spacing element has a thermal expansion coefficient substantially similar to the continuous diaphragm. This arrangement ensures that thermal stresses will be minimized between the two elements.

In a preferred embodiment, the semiconductor assembly is comprised of a plurality of emitters for irradiating the diaphragm with electromagnetic radiation and a plurality of detectors each having an output and each detector receiving a portion of the electromagnetic radiation which is reflected from the diaphragm and transducing the received radiation into a respectively associated electronic output signal. The continuous diaphragm is preferably generally planar having a rectangular boundary which has an opposing pair of long sides and an opposing pair of short sides. The plurality of emitters are preferably arranged generally in a row which is generally parallel to and spaced apart from one of the long sides of the diaphragm and the detectors are preferably arranged generally in a row spaced from the row of emitters and generally parallel to and spaced apart from one of the long sides of the diaphragm. Each emitter in the row of emitters is generally equally spaced apart from its adjacent neighbors and each detector in the row of detectors is generally equally spaced apart from its adjacent neighbors. The row of emitters is juxtaposed to the row of detectors such that any two adjacent detectors in the row of detectors lie equidistant from at least one common emitter in the row of emitters.

Each emitter preferably irradiates electromagnetic radiation in a beam field which when projected onto the diaphragm overlaps the projected beam field of its closest adjacent neighbors. Preferably, the electromagnetic radiation is selected from the group consisting of visible, infrared and ultraviolet light.

A portion of the semiconductor assembly (referencing portion) is used for irradiating electromagnetic radiation onto and detecting electromagnetic radiation reflected from a reference surface which does not move (i.e. is nonresponsive) with respect to tissue stress applied to the diaphragm. The reference surface is spaced apart from the diaphragm.

A current to voltage converter is respectively associated with the output of each detector for converting the current signal output by each respective detector to a voltage signal. A multiplexer is connected to the output of the converters for multiplexing their output to a central processing means wherein the data contained in the output signal of the converters is conditioned and processed.

Still further, the present invention provides a tissue contact stress sensor which generates a tissue contact stress signal indicative of the intra-arterial blood pressure of an arterial vessel and a correction signal for compensating for errors in the tissue contact stress signal caused by temperature drift and aging of the sensor. The system comprises a continuous diaphragm for placing against a patient's tissue which covers an underlying artery. The diaphragm is adapted to deform in response to stresses in the tissue overlaying the artery.

A semiconductor assembly is spaced apart from and placed in close proximity to the continuous diaphragm for directly irradiating the diaphragm with electromagnetic radiation and receiving a portion of the electromagnetic radiation irradiating from the continuous diaphragm. The semiconductor assembly converts the received radiation into a tissue contact stress signal (first signal) which represents blood pressure data whereby the quantity of electromagnetic radiation which is received by the semiconductor assembly is a function of the intra-arterial blood pressure. A spacing structure is coupled to the diaphragm and the semiconductor assembly thereby fixing the separation between the semiconductor assembly and the diaphragm. A referencing portion of the semiconductor assembly is spaced apart from and placed in close proximity to a wafer for directly irradiating a nonresponsive, reflective portion of the underside of the wafer with electromagnetic radiation and receiving a portion of the electromagnetic radiation reflected from the nonresponsive portion of the wafer. The referencing portion of the semiconductor assembly converts the received radiation into a second signal which represents reference data which is indicative of at least one reference factor whereby any change in the radiation received by the referencing portion of the semiconductor assembly is attributed to a change in at least one reference factor. The second signal is combined with the first signal in a manner which minimizes the dependence of the tissue contact stress data on the reference factors. The reference factors preferably include temperature of the sensor and effects due to sensor aging. The semiconductor assembly and the referencing portion of the semiconductor assembly are preferably fabricated from substantially the same materials and at substantially the same time and reside in substantially the same environment. This ensures that they track each other's age, temperature and other commonly shared environmental factors.

Still further the present invention provides a method for correcting errors in the output signal of a tissue contact stress sensor which are caused by the effects of aging and environmental factors on the sensor. The tissue contact stress sensor is of the type having an element for transducing blood pressure of a patient into a tissue stress signal. This method includes constructing a tissue contact stress sensor and a reference sensor from substantially identical materials at substantially the same time. The tissue contact stress sensor is adapted to be responsive to the tissue stress in the region of a superficial vessel and the reference sensor is adapted to be responsive to a fixed structural reference which does not vary with the tissue stress measured by the tissue contact stress sensor. The tissue contact stress sensor and a reference sensor are adapted to share the same environment so as to be equally influenced by aging, temperature and other environmental factors. Signals generated by the tissue contact stress sensor and a reference sensor are combined such that the errors caused by the effects of aging, temperature and other environmental factors are minimized.

Other advantages and meritorious features of the presentation will become more fully understood from the following description of the preferred embodiments, the appended claims and the drawings, a brief description of which follows.

DETAILED DESCRIPTION OF THE PREFERRED EMBODIMENTS

Figure 1:
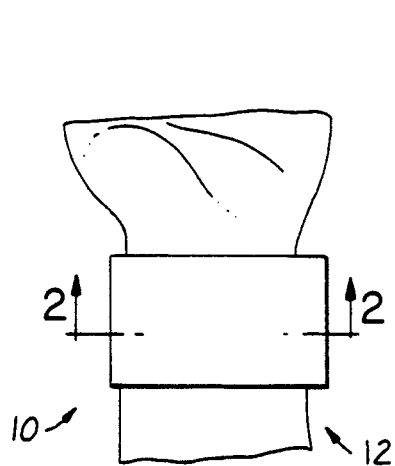
FIG. 1 is a plan view of the system of the present invention as applied to the wrist of a patient.

Now referring to the drawing of FIG. 1, arterial tonometer 10 is placed about wrist 12 of a patient for determining the patient's blood pressure. Arterial tonometer 10 measures the patient's intra-arterial blood pressure noninvasively by sensing the time varying surface tissue contact stresses in regions immediately over and in the vicinity of the artery of interest. In general, the artery to be measured must be superficial and overlaying relatively rigid structures. The arteries most commonly used are the radial artery in the wrist, the superficial temporal artery in the forehead the and the dorsalis pedis artery in the foot. For purposes of this disclosure, the radial artery in the wrist will be used as the main artery of discussion; however, the system of the present invention is equally applicable to any superficial artery which overlays a relatively rigid structure.

Figure 2:
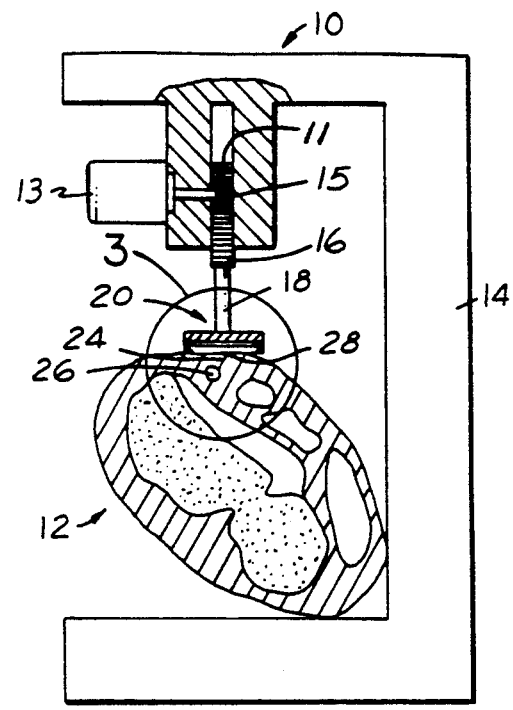
FIG. 2 is a cross-sectional view of the system of the present invention taken substantially along lines 2—2 of FIG. 1.

Now referring to the drawing of FIG. 2, arterial tonometer 10 comprises clamp body 14, rack 16, push arm 18 and sensor 20. Rack 16 is driven by motor 13 through pinion 11. Clamp 14 can take on any number of configurations and is shown here in a generic form. Motor 13 is adapted to rotate thereby rotating pinion 11 and moving rack 16. Any movement of rack 16 moves sensor 20 via push arm 18. When motor 13 is rotated in the appropriate direction, sensor 20 is forced against tissue 24 which overlays radial artery 26. The displacement caused by sensor 20 is adjusted to a level which properly applanates radial artery 26 without causing artery 26 to occlude.

An important element of the present invention is sensor 20 and its surrounding structure. Because sensor 20 is used to compress or applanate radial artery 26 during blood pressure measurement as well as measure the contact stress in tissue 24, the geometry of sensor 20 and its surrounding structure are vital to the proper conduction of stresses from radial artery 26 to tissue surface 28. A detailed discussion of sensor 20 and its associated structure now follows.

Figure 3:
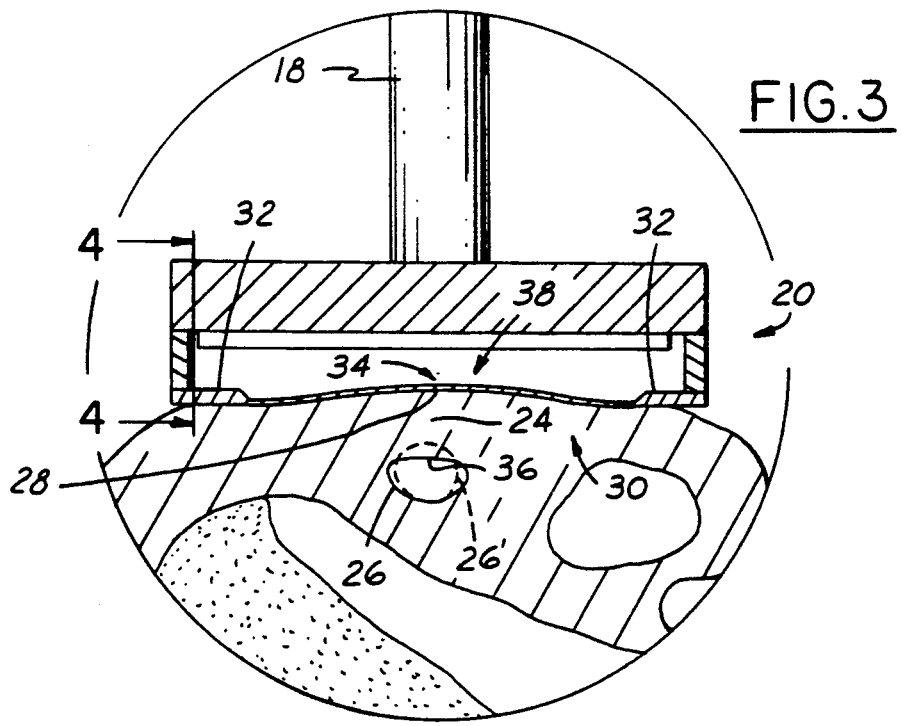
FIG. 3 is an amplified view of the system of the present invention taken substantially within encircled portion 3 of FIG. 2.

Now referring to the drawing of FIG. 3, sensor 20 includes wafer 30 which has a nonresponsive portion 32 and a responsive portion (diaphragm) 34. Nonresponsive portion 32 serves mainly to support and press responsive portion 34 upon tissue overlying radial artery 26. Under normal conditions when sensor 20 is not being applied to tissue 24, radial artery 26 has a generally rounded cross-section as depicted at 26'. As wafer 30 of sensor 20 is pressed upon tissue 24, radial artery 26' begins to applanate or flatten along its top surface 36, causing responsive portion 34 of wafer 30 to deflect slightly inward 38. As the blood pressure within radial artery 26 changes (i.e. pulsates), stress is created in tissue 24 which disturbs the equilibrium between responsive portion 34 of wafer 30 and top surface 28 of overlying tissue 24. This disturbance in equilibrium causes movement between diaphragm 34 and surface 24. Such movement exists until a new equilibrium is established. The ability of diaphragm 34 to move and assume a unique displacement position for a given blood pressure within radial artery 26 forms the fundamental mechanism whereby sensor 20 is able to transduce the intra-arterial pressure of radial artery 26. The details of sensor 20 will now be fully discussed.

Figure 4:
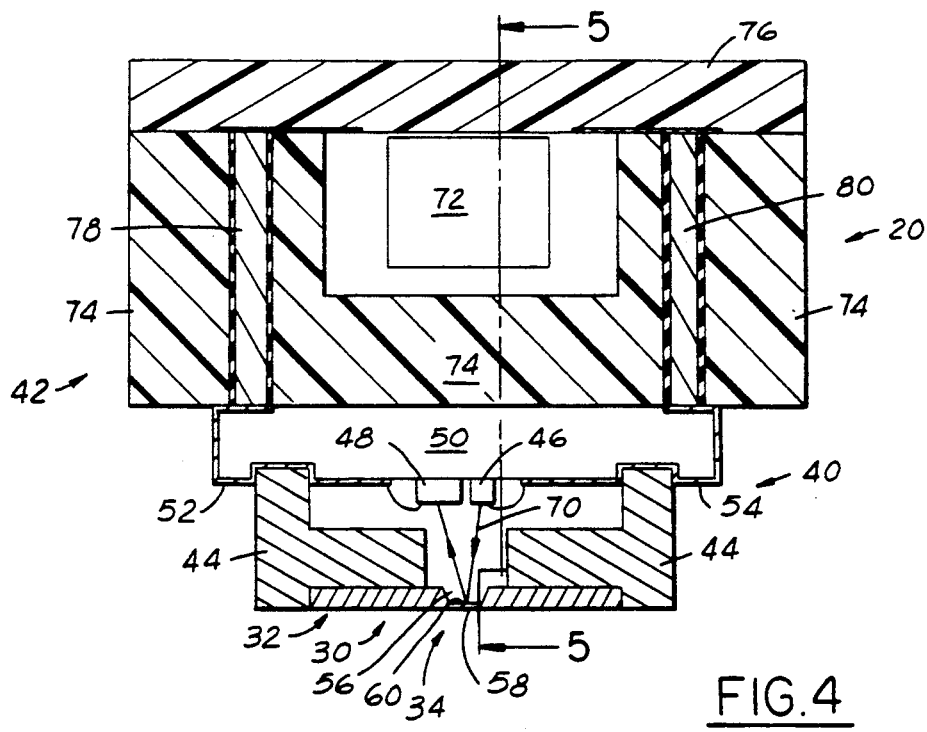
FIG. 4 is a cross-sectional view of the tissue contact stress sensor of the present invention taken substantially along lines 4—4 of FIG. 3.

Now referring to the drawing of FIG. 4, tissue contact stress sensor 20 is comprised of sensor head 40 and sensor base portion 42. Sensor head 40 comprises the transducer portion of sensor 20 and sensor base portion 42 includes electronic circuitry and other mechanical support structure necessary for properly operating sensor head 40. Sensor head 40 is generally comprised of six elements: sensor wafer 30, spacing structure 44, infrared emitting diodes (typified at 46), photo receivers (typified at 48), emitter/detector substrate 50 and circuit traces 52, 54.

An important feature of sensor 20 centers around the material and construction of sensor wafer 30. Sensor wafer 30 is formed from a wafer of single crystal silicon (SCS). Responsive diaphragm portion 34 of wafer 30 is formed by chemically micro-machining a trough 56 in the face of SCS wafer 30. This trough has a tetragonal-pyramidal geometry due to the crystal lattice structure of the SCS wafer 30. The bottom of the trough area 58 defines responsive diaphragm portion 34 of wafer 30. This portion defines a thin diaphragm region of highly controlled thickness and geometry. A major advantage in using SCS in the construction of diaphragm 34 is its superior engineering properties and its ability to be micro-machined which in turn provides a one-piece structure free of pre-stressing. Additional benefits in using SCS material include its ability to replicate small geometric features precisely and repeatedly, its linear elastic properties (i.e., almost no hysteresis) and its ability to quickly evidence its failed condition (under failure, the SCS diaphragm 34 totally fails thereby immediately evidencing its failed condition). This is to be contrasted with other materials which, under failure, do not fracture as does SCS but rather undergo inelastic deformation. Once the diaphragm undergoes inelastic deformation it loses its calibration but generally does not manifest its extreme, failed condition thereby usually going unnoticed.

Underside 60 of trough 56 is preferably metalized with a reflective material such as aluminum or gold. The thickness of the aluminum or gold is preferably generally 600 angstroms and its purpose will be explained shortly. Responsive portion 34 of wafer 30 changes its geometry with applied stress as a function of the material properties of the diaphragm. It is important to note that a coating of aluminum or gold generally 600 angstroms in thickness does not materially alter the properties of diaphragm portion 34 of wafer 30.

In the construction of tonometry sensors, the elasticity of responsive portion 34 of wafer 30 must be compatible with the characteristics of human tissue. If diaphragm surface 34 deforms excessively when responding to the stress of surface tissue 28, the tissue surface stress contour transduced by the sensor will be distorted, potentially affecting the accuracy of the measurement. Calculations, numerical simulation and experimental data have shown that diaphragm 34 of wafer 30 should be generally 50 times stiffer than that typical of tissue overlaying the artery of interest. The strain rate of the preferred embodiment is 0.24 micro-inch/mmHg measured at the midline of responsive diaphragm portion 34 of wafer 30.

Figures 6, 7A, 7B:
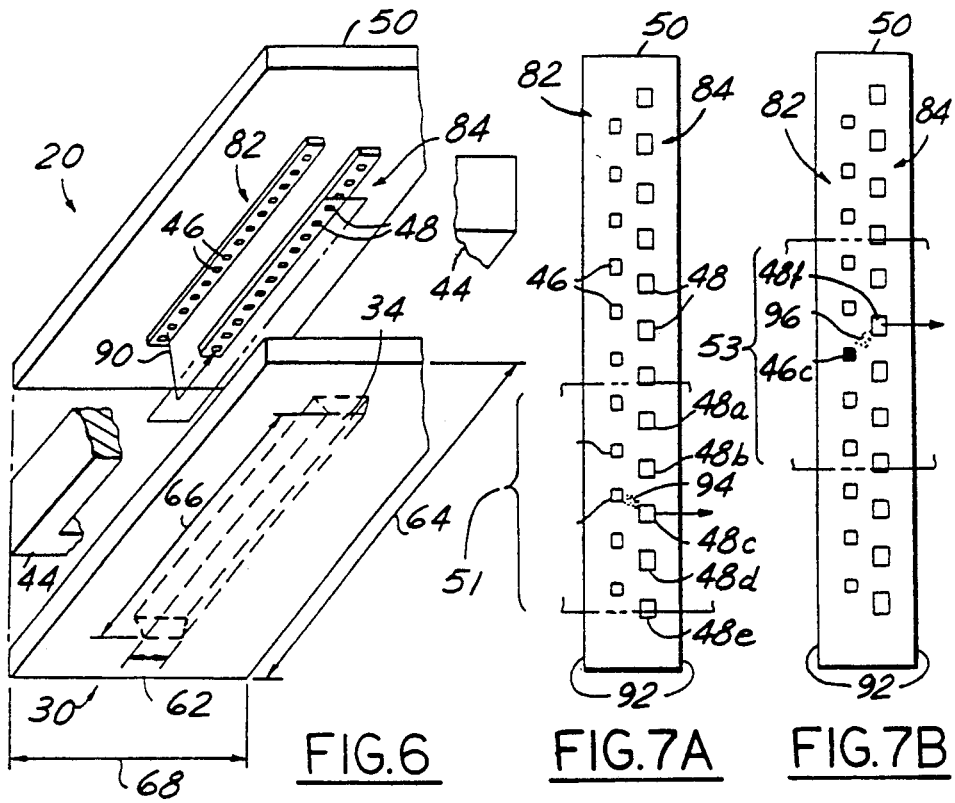
FIG. 6 is a partially exploded view of the tissue contact stress sensor of the present invention.
FIGS. 7a and 7b are diagrammatic views of the emitter and detector portions of the semiconductor assembly of the present ivention.

Now referring to the drawing of FIG. 4 and FIG. 6, width 62 of trough bottom 58 affects the maximum achievable spatial resolution and sensitivity. It has been empirically determined that width 62 is adequate for measurements in adult radial arteries when it is generally 0.020 inches. Narrower dimensions will generally be required for measurements in arteries smaller than adult radial arteries. The perimeter dimensions of wafer 30 play an important role in achieving accurate measurements. When used on an adult radial artery, the length 64 of wafer 30 must be sized so as to minimize interference with anatomical structures (e.g., the head of the radial bone laterally and medial radial tendon centrally) lying on either side of radial artery 26. Concurrently, length 66 of diaphragm 34 should be as long as possible in order to reduce sensitivity to lateral positioning and to allow measurement of contact stress in regions surrounding radial artery 26. It has been found that a wafer length 64 of generally 0.500 to 0.700 inches along with length 66 of diaphragm 34 being generally 0.35 to 0.45 inches is adequate to achieve these goals.

Choice of width 68 of wafer 30 affects the distribution of tissue forces. If width 68 is made too small, wafer 30 has a tendency to bend radial artery 26 at the perimeter of wafer 30 which in turn detrimentally affects the accuracy of the stress measurements. For the adult radial artery, a width 68 of generally 0.20 inches has been found suitable.

Spacing element 44 provides alignment and positioning of diaphragm 34 vis-a-vis array of emitters 46 and array of detectors 48. Spacing structure 44 is preferably manufactured from materials such as silicon nitride having a thermal coefficient of expansion similar to that of SCS (the preferred material to be used in the construction of wafer 30 and diaphragm 34). If a material is chosen for spacing structure 44 which does not have a similar thermal coefficient of expansion to that of SCS, the strains induced in diaphragm 34 would cause a small displacement in diaphragm 34 causing offset and sensitivity errors in the transduced signal.

Responsive portion 34 of wafer 30 provides a continuous mechanical displacement proportional to local surface tissue stress values. This displacement is sampled optically by an array of infrared emitting diodes (typified at 46) placed parallel to an array of photo detectors (typified at 48). Preferably, the photo detectors are either photo transistors or photo diodes. Diodes 46 receive their operational current through circuit traces typified at 54. Diodes 46 radiate electromagnetic energy 70 onto underside surface 60 of diaphragm 34. Electromagnetic energy 70 is reflected from underside 60 surface of trough 56 and falls upon photo receiver 48.

Photo receiver 48 transduces electromagnetic radiation 70 into an electric photo current signal which flows through circuit traces typified at 52 and is delivered to converter/multiplexer circuit 72. Substrate 50 forms the structural foundation upon which diodes 46 and photo receiver 48 are constructed. Support structure 74 connects sensor head 40 and all of its component parts to interconnect PC board 76. Compression connectors 78, 80 provide a convenient way of delivering power from multiplexing and power circuits 102 to emitter array 46 within head 40 and delivering transduced signals from detector array 48 to conversion circuits 100.

Figure 5:
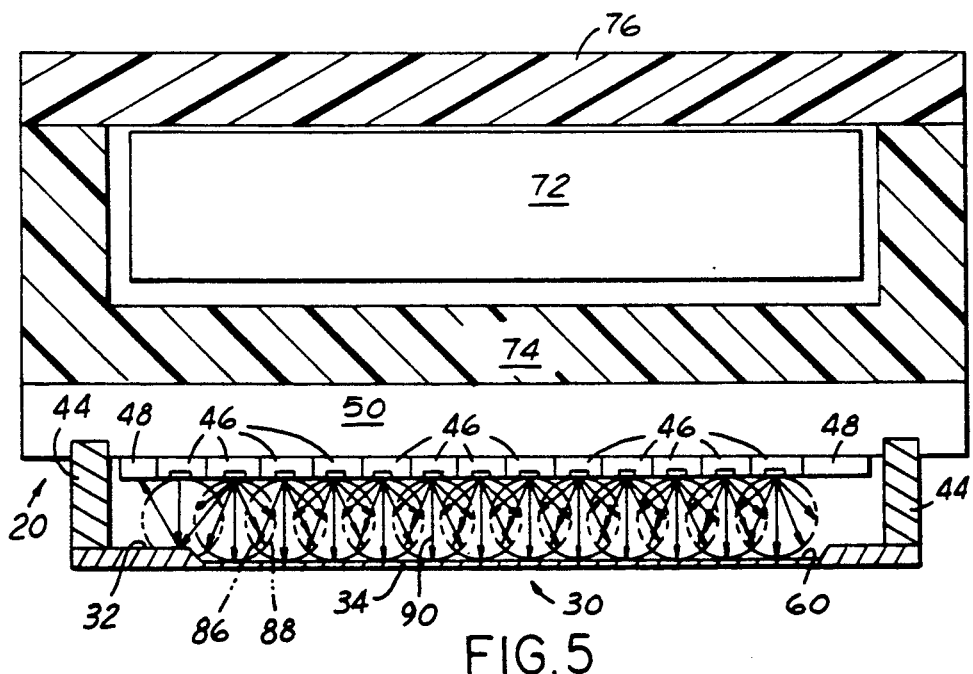
FIG. 5 is a cross-sectional view of the tissue contact stress sensor of the present invention taken substantially along lines 5—5 of FIG. 4.

Now referring to the drawing of FIG. 5 and FIG. 6, sensor 20 of the present invention includes wafer 30, spacer 44 and emitter/detector substrate 50. Wafer 30 includes nonresponsive portion 32 and responsive portion 34. Responsive portion 34 provides a continuous mechanical displacement proportional to local surface tissue stress values. This displacement is sampled optically by array 84 of photo detectors placed parallel to array 82 of emitters. Array 82 is preferably constructed from a plurality of individual, infrared emitting diodes 46 and array 84 of photo detectors is comprised of a plurality of individual photo detectors 48. Photo detectors 48 are preferably photo transistors or photo diodes. The beam field associated with each infrared diode (typical beam fields for two adjacent photo diodes 46 shown at 86, 88) is arranged to overlap the beam field of adjacent diodes 46. This overlapping technique produces spatially sampled outputs, which are spatially smoothed, from each opto electronic channel. These outputs collectively represent a continuous, spatially weighted integral of the deflection of responsive portion 34 of wafer 30.

The fundamental advantage offered by the continuous diaphragm approach is its ability to be monitored at any arbitrary location along its length and its inherent ability to spatially smooth the localized stress values. In addition to these advantages, the disclosed arrangement of emitter array 82 and sensor array 84 complements the diaphragm's properties by optically integrating the diaphragm's deformation over a finite region. Due to the overlapping beam fields 86, 88 of adjacent diodes 46, the measurement provided by each receiver 48 represents a spatially overlapping integral of the displacement of responsive portion 34 of wafer 30 in a region surrounding a diode/receiver pair. Preferably, a constant energy flux is radiated from each diode 46 with a Lambertian pattern (cosine law distribution) about an axis normal to the surface of each diode 46. A portion of this energy flux is reflected by the metalized coated underside 60 of responsive portion 34 of wafer 30 thereby striking one or more receivers 48 in the array of photo detectors 84. This in turn produces a photo current in each receiver 48 which is converted to a voltage by a current to voltage conversion circuit within converter/multiplexer circuit 72.

As diaphragm 34 responds to tissue stress, the electromagnetic radiation reflected from the active area of diaphragm 34 is dispersed. This action reduces the amount of radiation which would otherwise reach the neighboring receivers 48 and causes a reduction in their output signal. This dispersion of light rays 90 away from select receivers produces only a small deviation in the output signal of the select receivers (hereinafter referred to as the sensors inherent small signal current to total current ratio or small Isc/Itc ratio), and accordingly it is important to choose the geometric relationship of diode 46, receiver 48 and responsive portion 34 of wafer 30 to optimize the change of optical power received as a function of diaphragm displacement.

Although in the disclosed embodiments no device is shown disposed between diaphragm 34 and arrays 82, 84, it is contemplated that a device such as a lens or a mask, if so placed, may improve the sensors Isc/Itc ratio. For example, a thin opaque element (mask) could be placed between diaphragm 34 and arrays 82, 84 in a plane parallel to that of diaphragm 34. Windows could be placed through this element to allow energy from emitter array 82 to strike diaphragm 34 in a preferred region and be reflected to a preferred region of one (or more) detectors 48. To understand how the mask may improve the Isc/Itc ratio, it is helpful to first, consider how the unmasked version operates.

As the diaphragm bends, rays diverge away from select receivers 48 thereby reducing the amount of energy received as a function of the diaphragm curvature. In contrast, the mask could be designed so that as the diaphragm geometry (in the region where the beam strikes) changes with applied stress, the resulting reflected beam is partially blocked by the mask. This results in a more significant change in the amount of received energy per unit change in stress. The resulting improved Isc/Itc ratio improves signal quality and reduces the impact of thermal stresses and time degradation of the emitter and detector components.

As was mentioned above, even with the use of a mask, the inherent nature of the present invention limits the maximum achievable Isc/Itc ratio. Because of this fact, it is necessary to compensate for the variation in output signal caused by factors unrelated to blood pressure inasmuch as these factors could greatly compromise the accuracy of the system. Such factors may include the temperature dependence of the various optical and mechanical components which comprise sensor head 40, along with the variations experienced as the system ages. If these variables are not compensated for, unacceptable offset and gain errors could corrupt the accuracy of the sensor stress signal. To accomplish this compensation, one of the diode/receiver pairs are used to generate a reference signal by reflecting energy exclusively off nonresponsive portion 32 of diaphragm wafer 30. Inasmuch as this region is fixed, any variation in the photo current produced by the receiver 48 in this reference diode/receiver pair would be due to temperature, aging and environmental factors in array components 82, 84. This reference signal generated by reference receiver 48 is fed into the appropriate correction circuity (or software) which in turn performs the appropriate adjustment in the offset and gain and of each sensor channel as a function of the reference signal. An example of a methodology which could be employed to use the reference signal generated by the reference diode/receiver pair now follows.

The tonometer stress contact sensor of the present invention generates a plurality of electrical currents which are each a function of local diaphragm 34 deflection and local ambient temperature across the length of sensor head 40. First consider the simplest model of this sensor neglecting the contribution of temperature, and assume a linear relationship between output current and stress.

If p=the displayed value of pressure in mmHg, then $$p = SLOPE \cdot x + OFFSET$$

where SLOPE and OFFSET are calibration constants, and x is assumed to be a linear function of pressure.

For this model, the two calibration constants are calculated in software by substituting the desired values of p and the measured values of x for the following two known conditions:

0 mmHg applied to sensor,
120 mmHg applied to sensor.

However, the contribution of temperature to the sensor function is significant, and cannot be neglected. The simplest model of the function of pressure and temperature assumes that the OFFSET term is a linear function of temperature, and that the SLOPE term is a constant independent of temperature.

If we let d=the displayed value of pressure in mmHg, then, $$d = XSLOPE \cdot x + (RSLOPE \cdot r + OFFSET)$$

where XSLOPE, RSLOPE, and OFFSET are calibration constants, x is assumed to be a linear function of pressure and temperature and r is assumed to be a linear function of temperature.

The r input is derived from the reference sensor previously mentioned which has an opto electronic structure identical to that which generates the x input, except that it is not modulated by pressure. It is located such that it is in the same environment, and consequently, at the same temperature as the x opto electronics.

For this model, the three calibration constants are calculated in software by inserting the desired values of d and the measured values of x and r for the following three known conditions:

0 mmHg applied to sensor at temperature 1,
120 mmHg applied to sensor at temperature 1,
0 mmHg applied to sensor at temperature 2.

However, the effect of temperature on the SLOPE coefficient is also significant, and cannot be neglected. A model which also accounts for this effect, assuming it is linear, is constructed as follows:

$$d = [RXSLOPE \cdot r + XOFFSET] \cdot x + [RSLOPE \cdot r + OFFSET]$$

where d is the displayed value of pressure in mmHg, RXSLOPE, XOFFSET, RSLOPE, and OFFSET are calibration constants, x is assumed to be a linear function of pressure and temperature, and r is assumed to be a linear function of temperature.

For this model, the four calibration constants are calculated in software by inserting the desired values of d and the measured values of x and r for the following four known conditions:

0 mmHg applied to sensor at temperature 1, 120 mmHg applied to sensor at temperature 1, 0 mmHg applied to sensor at temperature 2, 120 mmHg applied to sensor at temperature 2.

A method of automatically performing these four calibrations in computer software, so that there is no interaction between conditions, i.e., calibration of any condition does not require recalibration of any previously calibrated condition, is as follows:

0 mmHg, temperature 1 cal:
From model, $$d = [RXSLOPE \cdot r + XOFFSET] \cdot x + [RSLOPE \cdot r + OFFSET] \quad (1)$$

and, since we expect to display 0 mmHg at p1 and t1, $$0 = [RXSLOPE \cdot r(t1) + XOFFSET] \cdot x(p1,t1) + [RSLOPE \cdot r(t1) + OFFSET] \quad (2)$$

Solving (2), $$OFFSET = -[RXSLOPE \cdot r(t1) + XOFFSET] \cdot x(p1,t1) - RSLOPE \cdot r(t1) \quad (3)$$

The input values are saved as:
R11 = r(t1)  X11 = x(p1,t1)
where
p1 = 0 mmHg applied pressure, and
t1 = temperature 1.
120 mmHg, temperature 1 cal:
Substituting the p2 and t1 conditions into (1)

$$120 = [RXSLOPE \cdot r(t1) + XOFFSET] \cdot x(p2,t1) + [RSLOPE \cdot r(t1) + OFFSET] \quad (4)$$

Subtracting (4)−(2), $$120 = [RXSLOPE \cdot r(t1) + XOFFSET] \cdot [x(p2,t1) - x(p1,t1)] \quad (5)$$

$$120 = [RXSLOPE \cdot r(t1) + XOFFSET] \cdot [x(p2,t1) - X11] \quad (6)$$

Solving (6), $$XOFFSET = 120 \div [x(p2,t1) - X11] - RXSLOPE \cdot r(t1) \quad (7)$$

Readjusting OFFSET from (3), $$OFFSET = -[RXSLOPE \cdot R11 + XOFFSET] \cdot X11 - RSLOPE \cdot R11 \quad (8)$$

The input values are saved as:
R21 = r(t1)
X21 = x(p2,t1)
where
p2 = 120 mmHg applied pressure, and
t1 = temperature 1.
0 mmHg, temperature 2 cal:
Substituting the p1 and t2 conditions into (1), $$0 = [RXSLOPE \cdot r(t2) + XOFFSET] \cdot x(p1,t2) + [RSLOPE \cdot r(t2) + OFFSET] \quad (9)$$

Subtracting (9)−(2), $$0 = RXSLOPE \cdot [r(t2) \cdot x(p1,t2) - r(t1) \cdot x(p1,t1)] + XOFFSET \cdot [x(p1,t2) - x(p1,t1)] + RSLOPE \cdot [r(t2) - r(t1)] \quad (10)$$

Solving (10), $$RSLOPE = -\{RXSLOPE \cdot [r(t2) \cdot x(p1,t2) - R11 \cdot X11] + XOFFSET \cdot [x(p1,t2) - x11]\} \div \{r(t2) - R11\} \quad (11)$$

Readjusting OFFSET from (3), $$OFFSET = -[RXSLOPE \cdot R11 + XOFFSET] \cdot X11 - RSLOPE \cdot R11 \quad (12)$$

The input values are saved as:
R12 = r(t2)
X12 = x(p1,t2)
where
p1 = 0 mmHg applied pressure, and
t2 = temperature 2.
120 mmHg, temperature 2 cal:
Substituting the p2 and t2 conditions into (1), $$120 = [RXSLOPE \cdot r(t2) + XOFFSET] \cdot x(p2,t2) + [RSLOPE \cdot r(t2) + OFFSET] \quad (13)$$

Subtracting (13)−(9), $$120 = [RXSLOPE \cdot r(t2) + XOFFSET] \cdot [x(p2,t2) - x(p1,t2)] \quad (14)$$

$$= [RXSLOPE \cdot r(t2) + XOFFSET] \cdot [x(p2,t2) - X12]$$

$$RXSLOPE \cdot r(t2) + XOFFSET = 120 \div [x(p2,t2) - X12] \quad (15)$$

From (7) and (8), $$XOFFSET = [120 \div \{x21 - x11\}] - RXSLOPE \cdot R21 \quad (16)$$

Substituting (16) into (15), $$RXSLOPE \cdot [r(t2) - R21] = [120 \div \{x(p2,t2) - X12\}] - [120 \div \{x21 - x11\}]$$

$$RXSLOPE = [120 \div \{r(t2) - R21\}] \cdot [[1 \div \{x(p2,t2) - x12\}] - [1 \div \{x21 - x11\}]] \quad (17)$$

Readjust XOFFSET by computing from (16) with the new value of RXSLOPE inserted.
Readjust RSLOPE from (11) with the new values of RXSLOPE and XOFFSET inserted.
Readjust OFFSET from (12) with the new values of RXSLOPE, XOFFSET, and RSLOPE inserted.
The function of the calibration points, in the order discussed above, is as follows:
Point 1: Set pressure offset (zero point).
Point 2: Set pressure slope (gain).
Point 3: Set offset (zero point) compensation.
Point 4: Set slope (gain) compensation.
As can be seen from the above method, there is no interaction between the calibration points. The points may be calibrated in any order, and not all points need be calibrated. For example, if operation will only occur at temperature 1, only the first two points need be calibrated. If only the offset needs to be corrected, the first point calibration is sufficient. If only the full scale point at temperature 1 needs correction, only the second point need be calibrated.

Now referring to the drawings of FIGS. 7a and 7b, diode array 82 is arranged such that each diode 46 in the array of diodes 82 is generally arranged in a straight row substantially parallel to a long side 92 of electronic substrate 50. Likewise, each receiver 48 in the array of receivers 84 is generally arranged in a straight row which is substantially parallel to a long side 92 of electronic substrate 50. Row of diodes 46 is spaced apart from the row of receivers 48 and each diode 46 is juxtaposed with two receivers 48 such that it lies generally equidistant from its two closest receivers 48. This generally equidistant (or offset) relationship is demonstrated in FIG. 7a by virtue of emitter 46a being generally equidistant from its two closest detector neighbors 48a, 48b. Although this equidistant relationship has some advantages, which are discussed below, it is believed that other arrangements between emitters and detectors may also work effectively.

Coordination of the activation and monitoring of selected diode/receiver pairs together with the offset geometry between diodes 46 and receivers 48 allows a higher effective spatial resolution than can be achieved by using the same number of diode/receiver pairs which are horizontally matched in a one-to-one configuration across the entire length of electronic substrate 50. Due to the disclosed diagonal spacing of diode-/receiver pairs, the effective spatial resolution of sensor 20 is effectively doubled in comparison to the resolution achievable using horizontally matched diode/receiver pairs. A similar approach could be used if the elements were aligned without offsetting; however, this would result in nonequal reflective angles and measurement regions being produced for alternate interrogation sites.

In the example shown in FIG. 7a, if an artery of interest (outlined at 51) spans receivers 48a–48e, it would be generally centered about location 94. One or more emitters within emitter array 82 may be used with one or more detectors within detector array 84 to form a select group of emitter/detectors for detecting tissue stress. Likewise, in reference to FIG. 7b, if the artery of interest (outlined at 53) appeared centered about location 96, one or more emitters may be used in conjunction with one or more detectors to detect tissue stress.

Figure 8:
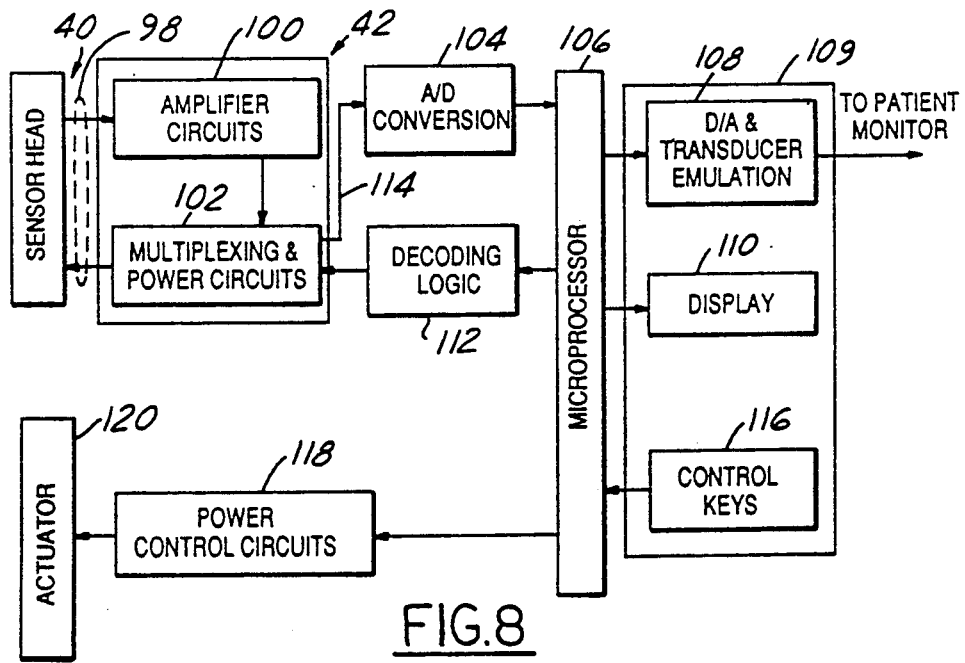
FIG. 8 is an electronic block diagram of the tissue contact stress sensor of the present invention.

Now referring to the drawing of FIG. 8, sensor head 40 is electronically coupled via multiple communication lines 98 to sensor base portion 42. Sensor base portion 42 provides conversion circuitry 100 to convert the current output signals from the array of detectors 84 to voltage output signals. These voltage signals are sent through multiplexer 102 where they are selectively digitized by A/D converter 104 and passed along to microprocessor 106. Microprocessor 106 performs the error correction spoken of earlier in the application and can also perform various other data compilation/analysis tasks. The blood pressure data can then be sent to any number of outputs such as a digital to analog converter 108 in cases where an analog representation of blood pressure is desirable. Blood pressure data may also be sent to display device 110 where it can provide the user with a continuously updated digital readout of blood pressure. Microprocessor 106 can be programmed to control decoding logic circuitry 112 which in turn activates select power circuits within multiplexing and power circuits 102.

The user of the system of the present invention can be given certain control options which can be input to microprocessor 106 via control keys 116. Power control circuit 118 can be used to interface microprocessor 106 to any number of mechanical actuators 120 which may be used to respond to various commands from microprocessor 106 in the utilization of sensor 40. For example, a routine may be used by microprocessor 106 which periodically queries whether sensor head 40 is properly applanating the artery of interest. If it is determined that the artery of interest is not properly applanated by wafer 30, microprocessor 106 may activate power control circuit 118 to command actuator 120 to move sensor 20 such that it properly applanates the artery of interest. Other applications may be devised where it is desirable to move, or otherwise control sensor head 20.

Figure 9:
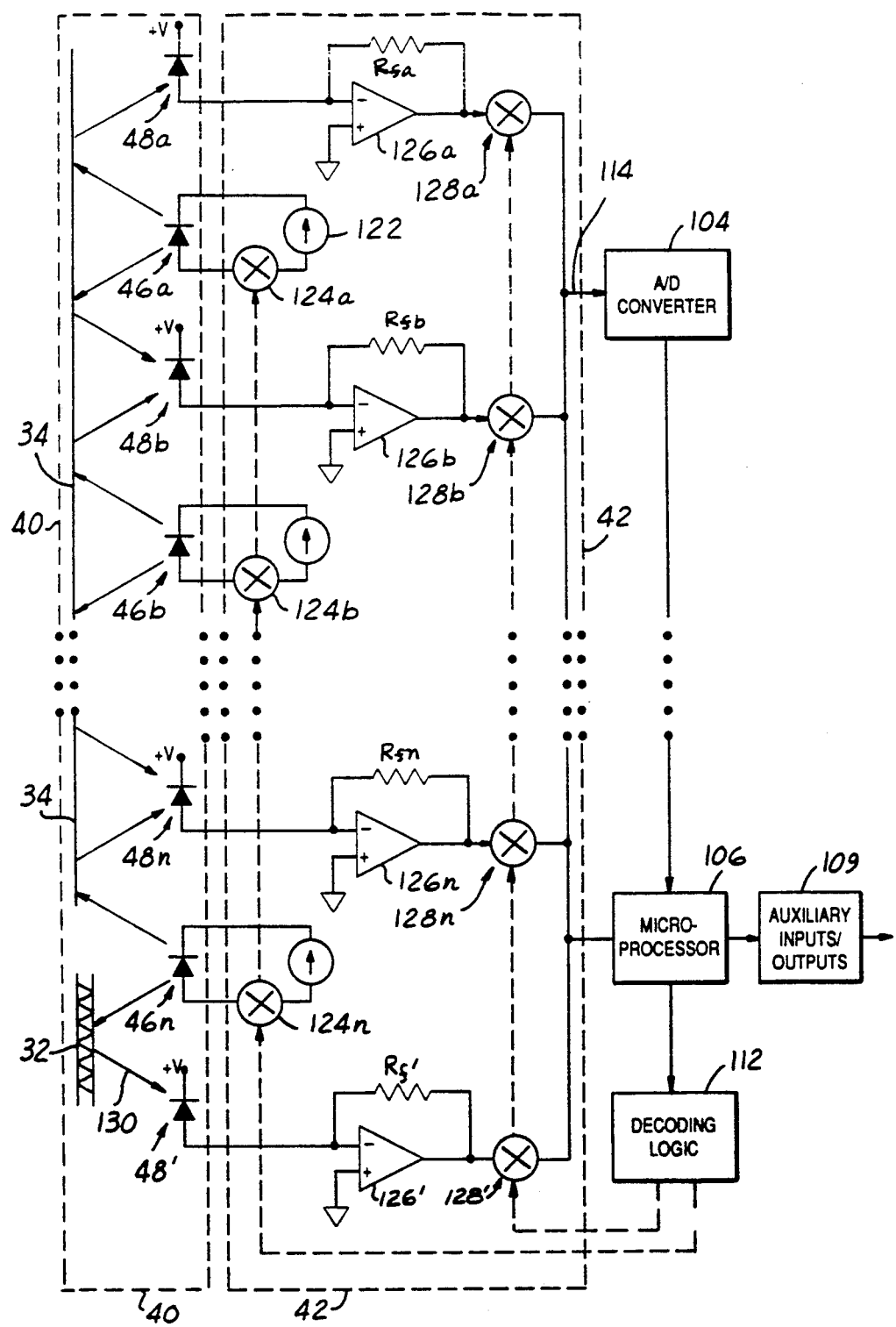
FIG. 9 is a detailed schematic of the block diagram of FIG. 8.

Now referring to the drawing of FIG. 9, sensor head 40 is comprised of a continuous responsive diaphragm portion 34 which reflects light from diodes 46(a–n) and onto receivers 48(a–n). Each diode 46 is fed by current source typified at 122 which can be selectively switched on and off via a respective switch 124(a–n). These switches 124a through 124n are all individually controlled via decoding logic circuit 112. This is the fundamental mechanism whereby each diode 46a through 46n can be selectively activated to determine what portion of diaphragm 34 is best suited to be used to transduce the tissue stress signal. Each receiver 48a through 48n receives a portion of the light reflected from diaphragm 34 and converts this reflected light into an electrical current signal which is converted to a voltage by each receiver's respective converter 126a through 126n. Converters 126a through 126n are configured as current to voltage converters which effect a linear current-to-voltage conversion of the current signal derived from the respective receiver. Current-to-voltage converter circuits are well known to those skilled in the art and, accordingly, will not be discussed in detail here. The output of each converter is made available to its respective switch 128a through 128n. Switches 128a through 128n are controlled via decoding logic 112 which enables microprocessor 106 to select any output from converter 126a through 126n and place it on line 114 where it is digitized by A/D converter 104.

One detector 48' is adapted to receive light 130 which is reflected from nonresponsive portion 32 of wafer 30. As has previously been discussed, detector 48' is used to generate a reference signal which will be used by microprocessor 106 to compensate for offset and gain errors due to temperature, aging and other environmental factors.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. Accordingly, it is to be understood that the subject matter sought to be afforded protection hereby should be deemed to extend to the subject matter defined in the appended claims, including all fair equivalents thereof.

I claim:

1. For use in a system for noninvasively determining the intra-arterial blood pressure of a patient, a tissue contact stress sensing apparatus comprising:
   a wafer having a continuous diaphragm for placing against a patient's tissue which covers an underlying artery, said diaphragm adapted to be deformed in response to stress in said tissue caused by the intra-arterial blood pressure of said artery,
   semiconductor assembly means placed in close proximity to and spaced apart from said continuous diaphragm for directly,
   irradiating said diaphragm with electromagnetic radiation,
   receiving a portion of said electromagnetic radiation reflected from said continuous diaphragm, and
   whereby the quantity of electromagnetic radiation received by said semiconductor assembly means is a function of the displacement of said continuous diaphragm in response to said tissue stress caused by said intra-arterial blood pressure of said artery.

2. The tissue contact stress sensing apparatus of claim 1 wherein said diaphragm is comprised of silicon.

3. The tissue contact stress sensing apparatus of claim 2, wherein said diaphragm is comprised of single crystal silicon.

4. The tissue contact stress sensing apparatus of claim 2, wherein said wafer is comprised of silicon and has a longitudinal trough therein and, wherein the bottom of said trough forms one side of said diaphragm.

5. The tissue contact stress sensing apparatus of claim 4, wherein said longitudinal trough has a cross-sectional profile generally resembling a tetragonal-pyramidal geometry.

6. The tissue contact stress sensing apparatus of claim 4, wherein said trough has a generally planar bottom.

7. The tissue contact stress sensing apparatus of claim 1, wherein said wafer has a longitudinal trough therein and, wherein the bottom of said trough forms one side of said diaphragm, and wherein said trough bottom is coated with a reflective material for reflecting the electromagnetic radiation irradiated by said semiconductor assembly means.

8. The tissue contact stress sensing apparatus of claim 7, wherein said trough bottom is generally $6.5 \times 10^{-6}$ meters thick.

9. The tissue contact stress sensing apparatus of claim 7, wherein said trough bottom is coated with metal.

10. The tissue contact stress sensing apparatus of claim 9, wherein said metal is selected from the group consisting of gold or aluminum.

11. The tissue contact stress sensing apparatus of claim 9, wherein said metal coating is generally 600 angstroms thick.

12. The tissue contact stress sensing apparatus of claim 1, wherein said diaphragm has an effective stiffness which is sufficient to prevent significant distortion of the stress information contained within the received electromagnetic radiation.

13. The tissue contact stress sensing apparatus of claim 1, wherein said continuous diaphragm has a strain rate of generally 0.24 micro-inch/mmHg.

14. The tissue contact stress sensing apparatus of claim 1, wherein said diaphragm has two opposing longitudinal sides spaced generally 0.020 inches apart.

15. The tissue contact stress sensing apparatus of claim 1, wherein said wafer has a generally rectangular face for placing against said tissue overlying said artery, said face having a first and second set of opposing parallel sides, wherein said first set of opposing sides of said rectangular face are generally 0.577 inches apart, and wherein said diaphragm is bounded by at least two generally parallel sides spaced generally 0.425 inches apart.

16. The tissue contact stress sensing apparatus of claim 15, wherein said second set of opposing parallel sides of said face are generally 0.200 inches apart.

17. The tissue contact stress sensing apparatus of claim 1 further including a spacer element disposed between said wafer and said semiconductor assembly means and wherein said spacer element, diaphragm, wafer and semiconductor assembly means all have a substantially similar thermal expansion coefficient for minimizing thermally induced drift and offset errors.

18. The tissue contact stress sensing apparatus of claim 17, wherein said spacing element is comprised of silicon nitride.

19. The tissue contact stress sensing apparatus of claim 1, wherein said semiconductor assembly means is comprised of a plurality of emitters for irradiating said diaphragm with electromagnetic radiation, and a plurality of detectors each having an output, each detector receiving a portion of said electromagnetic radiation and transducing said received radiation into a respectively associated electronic current output signal.

20. The tissue contact stress sensing apparatus of claim 19, wherein said continuous diaphragm is generally planar having a rectangular boundary, said boundary having an opposing pair of long sides and an opposing pair of short sides.

21. The tissue contact stress sensing apparatus of claim 20, wherein said plurality of emitters are arranged generally in a row which is generally parallel to and spaced apart from one of said long sides of said diaphragm, and wherein said detectors are arranged generally in a row separate from said row of emitters, and generally parallel to and spaced apart from one of said long sides of said diaphragm.

22. The tissue contact stress sensing apparatus of claim 21, wherein said emitters are generally equally spaced apart from one another and said detectors are generally equally spaced apart from one another, and wherein said row of emitters is juxtaposed to said row of detectors such that any two adjacent detectors in said row of detectors lie equidistant from at least one common emitter in said row of emitters.

23. The tissue contact stress sensing apparatus of claim 19, wherein each emitter in said plurality of emitters irradiates electromagnetic radiation in a beam field which when projected onto said diaphragm, overlaps the projected beam field of its closest adjacent neighbors.

24. The tissue contact stress sensing apparatus of claim 19, wherein said electromagnetic radiation is selected from the group consisting of visible, infrared and ultraviolet light.

25. The tissue contact stress sensing apparatus of claim 19, further comprising converter means, coupled to the outputs of said detectors, for converting said electric current signal output by each detector into an electric voltage signal.

26. The tissue contact stress sensing apparatus of claim 25, further comprising multiplexing means and central processing means, said multiplexing means coupled to said converter means for selecting one of said converted electronic signals and transferring said signal to said central processing means for analysis.

27. The tissue contact stress sensing apparatus of claim 1, wherein said semiconductor assembly means includes a portion for irradiating electromagnetic radiation onto and detecting electromagnetic radiation reflected from a reference surface, said reference surface spaced apart from said diaphragm.

28. The tissue contact stress sensing apparatus of claim 27, wherein said semiconductor assembly means and said portion of said semiconductor assembly means are fabricated from substantially the same materials and reside in close proximity to each other.

29. The tissue contact stress sensing apparatus of claim 28, wherein said electromagnetic radiation is selected from the group consisting of visible, infrared and ultraviolet light.

30. For use in a system for noninvasively determining the intra-arterial blood pressure of a patient, a tissue contact stress sensor for generating a tissue contact stress signal indicative of said intra-arterial blood pressure and a correction signal for compensating for errors in said tissue contact stress signal caused by temperature drift and aging of said sensor, said system comprising:

a wafer having a continuous diaphragm and a nonresponsive portion, said continuous diaphragm for placing against a patient's tissue which covers an underlying artery, said diaphragm adapted to be deformed in response to said intra-arterial blood pressure of said artery, semiconductor assembly means spaced apart from and placed in close proximity to said continuous diaphragm for directly, irradiating said diaphragm with electromagnetic radiation, receiving a portion of said electromagnetic radiation reflected from said continuous diaphragm, converting said received radiation into a tissue contact stress signal which represents blood pressure data whereby the quantity of electromagnetic radiation which is received by said semiconductor assembly means is a function of the displacement experienced by said continuous diaphragm in response to said intra-arterial blood pressure of said artery, spacing structure coupled to said nonresponsive portion of said wafer and said semiconductor assembly means, said spacing structure fixing said separation between said semiconductor assembly means and said wafer, a portion of said semiconductor assembly means, spaced apart from and placed in close proximity to said nonresponsive portion of said wafer for directly, irradiating said nonresponsive portion of said wafer with electromagnetic radiation, receiving a portion of said electromagnetic radiation reflected from said nonresponsive portion of said wafer, converting said received radiation into a correction signal which represents reference data which is indicative of at least one reference factor, and whereby any change in the radiation received by said portion of said semiconductor assembly means is attributed to at least one of said reference factors and whereby said correction signal is combined with said tissue contact stress signal in a manner which minimizes the dependence of said blood pressure data on at least one of said reference factors.

31. The tissue contact stress sensor of claim 30, wherein said reference factors include temperature and aging of said wafer, semiconductor assembly means and spacing structure.

32. The tissue contact stress sensor of claim 30, wherein said semiconductor assembly means and said portion of said semiconductor assembly means are fabricated from substantially the same materials and at substantially the same time and said materials reside in close proximity to each other.

33. The tissue contact stress sensor of claim 30, wherein said diaphragm is comprised of single crystal silicon.

34. The tissue contact stress sensor of claim 33, wherein said spacing structure is comprised of silicon nitride.

35. The tissue contact stress sensor of claim 30, wherein said electromagnetic radiation is selected from the group consisting of visible, infrared, and ultraviolet light.

36. The tissue contact stress sensor of claim 30, wherein said diaphragm is comprised of a silicon base having a longitudinal trough therein.

37. The tissue contact stress sensor of claim 36, wherein said trough has a generally planar bottom.

38. The tissue contact stress sensor of claim 37, wherein said trough bottom is generally $6.5 \times 10^{-6}$ meters thick.

39. A method for correcting errors in the output signal of a tissue contact stress sensor, said errors caused by the effects of aging and environmental factors on said sensor, said tissue contact stress sensor of the type having an element for placing against a patient's tissue covering an artery of interest, said element responsive to tissue stress, comprising the steps of:

constructing a tissue contact stress sensor and a reference sensor from substantially identical materials at substantially the same time, adapting said tissue contact stress sensor to be responsive to said element, adapting said reference sensor to be responsive to a fixed reference source which does not vary with said tissue contact stress measured by said tissue contact stress sensor, whereby an output signal of said reference sensor only changes as a function of said reference sensor aging, temperature and environmental factors, adapting said tissue contact stress sensor and said reference sensor to share the same environment so as to be equally influenced by aging and environmental factors, and combining the output signals generated by said tissue contact stress sensor and said reference sensor in a way which removes said influence of aging and environmental factors from said output of said tissue contact stress sensor.

40. For use in a system for noninvasively determining the intra-arterial blood pressure of a patient, a miniaturized tissue contact stress sensing apparatus comprising:

a silicon wafer having a nonresponsive portion and a continuous silicon diaphragm portion, said continuous silicon diaphragm portion for placing against a patient's tissue which covers an underlying artery, said diaphragm adapted to be responsive to stress in said tissue caused by blood pressure pulsations in said underlying artery, integrated circuit means placed in close proximity to and spaced apart from said continuous diaphragm for directly, irradiating said diaphragm with electromagnetic radiation, receiving a portion of said electromagnetic radiation reflected from said continuous diaphragm, and whereby the quantity of electromagnetic radiation received by said integrated circuit means is a function of the tissue stress sensed by said continuous diaphragm, said tissue stress resulting from blood pressure pulsations in said underlying artery.

41. The tissue contact stress sensing apparatus of claim 40, wherein said diaphragm is comprised of single crystal silicon.

42. The tissue contact stress sensing apparatus of claim 40, wherein said wafer has a longitudinal trough therein and wherein the bottom of said trough forms one side of said diaphragm and wherein said longitudinal trough has a cross-sectional profile generally resembling a tetragonal-pyramidal geometry.

43. The tissue contact stress sensing apparatus of claim 42, wherein said trough has a generally planar bottom and wherein said trough bottom is coated with a material for reflecting the electromagnetic radiation irradiated by said integrated circuit means.

44. The tissue contact stress sensing apparatus of claim 43, wherein said trough bottom is generally $6.5 \times 10^{-6}$ meters thick.

45. The tissue contact stress sensing apparatus of claim 43, wherein said trough bottom is coated with metal and wherein said metal is selected from the group consisting of gold or aluminum and wherein said metal coating is generally 600 angstroms thick.

46. The tissue contact stress sensing apparatus of claim 40, wherein said diaphragm has an effective stiffness of generally fifty times greater than that typical of said tissue over laying said artery.

47. The tissue contact stress sensing apparatus of claim 40, wherein said continuous diaphragm has a strain rate of generally 0.24 micro-inch/mmHg.

48. The tissue contact stress sensing apparatus of claim 40, wherein said diaphragm has two opposing longitudinal sides spaced generally 0.020 inches apart.

49. The tissue contact stress sensing apparatus of claim 40, wherein said wafer has a generally rectangular face for placing against said tissue overlying said artery, said face having a first and second set of opposing parallel sides, wherein said first set of opposing sides of said rectangular face are generally 0.577 inches apart, and wherein said diaphragm is bounded by at least two generally parallel sides spaced generally 0.425 inches apart and wherein said second set of opposing parallel sides of said face are generally 0.200 inches apart.

50. The tissue contact stress sensing apparatus of claim 40, further including a spacing element disposed between said continuous diaphragm and said integrated circuit means for providing alignment and positioning of said integrated circuit means in relation to said diaphragm and wherein said spacing element has a thermal expansion coefficient substantially similar to that of said continuous diaphragm and wherein said spacing element is comprised of silicon nitride.

51. The tissue contact stress sensing apparatus of claim 40, wherein said integrated circuit means is comprised of a plurality of emitters for irradiating said diaphragm with electromagnetic radiation, and a plurality of detectors each having an output, each detector receiving a portion of said electromagnetic radiation and transducing said received radiation into a respectively associated electric current output signal.

52. The tissue contact stress sensing apparatus of claim 51, wherein said continuous diaphragm is generally planar having a rectangular boundary, said boundary having an opposing pair of long sides and an opposing pair of short sides and wherein said plurality of emitters are arranged generally in a row which is generally parallel to and spaced apart from one of said long sides of said diaphragm, and wherein said detectors are arranged generally in a row separate from said row of emitters, and generally parallel to and spaced apart from one of said long sides of said diaphragm.

53. The tissue contact stress sensing apparatus of claim 52, wherein said emitters are generally equally spaced apart and said detectors are generally equally spaced apart, and wherein said row of emitters is juxtaposed to said row of detectors such that any two adjacent detectors in said row of detectors lie equidistant from at least one common emitter in said row of emitters.

54. The tissue contact stress sensing apparatus of claim 51, wherein each emitter in said plurality of emitters irradiates electromagnetic radiation in a beam field which when projected onto said diaphragm, overlaps the projected beam field of its closest adjacent neighbors.

55. The tissue contact stress sensing apparatus of claim 51, wherein each emitter radiates electromagnetic energy which follows a Lambertian pattern about an axis normal to an emitting surface of said emitter and wherein said electromagnetic radiation is selected from the group consisting of visible, infrared and ultraviolet light.

56. The tissue contact stress sensing apparatus of claim 51, further comprising converter means coupled to the outputs of said detectors for converting said electric current signal output by each detector into and electric voltage signal and further comprising multiplexing means and central processing means said multiplexing means coupled to said converter means for selecting one of said converted electronic signals and transferring said signal to said central processing means for processing.

57. The tissue contact stress sensing apparatus of claim 40, wherein said integrated circuit means further includes a referencing portion for irradiating electromagnetic radiation onto and detecting electromagnetic radiation reflected from a surface of said nonresponsive portion of said silicon wafer, said nonresponsive wafer surface spaced apart from said diaphragm and wherein said integrated circuit means and said referencing portion of said integrated circuit means are fabricated from substantially the same materials and reside in close proximity to each other and wherein said electromagnetic radiation is selected from the group consisting of visible, infrared and ultraviolet light.

* * * * *